United States Patent [19]

Horton et al.

[11] Patent Number: 5,726,115

[45] Date of Patent: Mar. 10, 1998

[54] BRIDGED BIS-AMINO GROUP 4 METAL COMPOUNDS IN A CATALYST COMPOSITION FOR THE PRODUCTION OF ALPHA-OLEFINS

[75] Inventors: Andrew David Horton; Jan De With, both of Amsterdam, Netherlands

[73] Assignee: Shell Oil Company, Houston, Tex.

[21] Appl. No.: 615,551

[22] Filed: Mar. 11, 1996

[30] Foreign Application Priority Data

Mar. 8, 1995 [EP] European Pat. Off. .............. 98200570

[51] Int. Cl.⁶ .............................. B01J 31/00; B04J 37/00; C08F 4/02; C08F 4/60
[52] U.S. Cl. .................. 502/152; 502/118; 502/129; 502/128; 502/153; 502/155; 502/156; 502/202; 502/103; 526/126; 526/127; 526/133; 526/139; 556/22; 556/52; 556/56; 556/18
[58] Field of Search .................... 502/152, 153, 502/155, 156, 118, 124, 129, 202; 526/22, 52, 56

[56] References Cited

U.S. PATENT DOCUMENTS

| 5,387,568 | 2/1995 | Ewen et al. ........................ 502/152 |
| 5,434,115 | 7/1995 | Yamada et al. ..................... 502/152 |

FOREIGN PATENT DOCUMENTS

| WO 92/12162 | 7/1992 | WIPO . |
| WO 96/27439 | 9/1996 | WIPO . |

OTHER PUBLICATIONS

D.J. Brauer et al., J. Organomet. Chem., vol. 150, pp. 215–231, May 1978.
U. Zucchini et al., J. Organomet. Chem., vol. 26, pp. 357–372, 1971.

Primary Examiner—Glenn Caldarola
Assistant Examiner—J. Pasterczyk

[57] ABSTRACT

A catalyst composition comprising a bis-amide compound represented by the formula

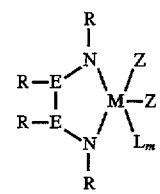

wherein M is zirconium, hafnium or titanium; each N is a three coordinate nitrogen atom; each e is Si, Ge or Sn; each Z is, independently, a hydride or R; each R is, independently, a hydrocarbyl one or more carbon atoms of which may be substituted by an element selected from Si, O, P, N and S; L is a neutral Lewis base and m is a number from 0 to 2; or a dimer thereof and a second component. Preferably the second component is a compound which is capable of providing a bulky and labile anion $[A]^-$, which anion is substantially non-coordinating under the reaction conditions and contains at least one boron atom. Also provided is a process for oligomerizing or co-oligomerizing alpha olefins in the presence of this catalyst composition.

9 Claims, No Drawings

BRIDGED BIS-AMINO GROUP 4 METAL COMPOUNDS IN A CATALYST COMPOSITION FOR THE PRODUCTION OF ALPHA-OLEFINS

FIELD OF THE INVENTION

This invention relates to a novel catalyst composition and to its use in the oligomerization and co-oligomerization of one or more alkenes (olefins), in particular alpha olefins. More in particular, the invention relates to the oligomerization of ethene to higher olefins, that is to olefins having 4–24 carbon atoms. The product higher olefins, in particular linear alpha olefins having 6–10 carbon atoms, are in great demand as intermediates in the preparation of detergents, lubricant additives and polyolefins. However, the oligomerization reaction also produces less valuable products, such as internal olefins and branched olefins and olefins having a number of carbon atoms outside the range of 4–24. By further processing, these latter products can be converted to the desired linear alpha olefins.

BACKGROUND OF THE INVENTION

Polymerization processes of olefins, such as the production of polyethylene from ethene, whereby homogeneous catalyst systems of the Ziegler-Natta type are used, are well known. Oligomerization processes of lower olefins to higher olefins are also well known. In these processes use is made of varying catalyst systems. For example, from GB-A-135873 it is known that, $C_4$–$C_{20}$ linear alpha olefins can be prepared from ethene by oligomerization in the presence of a catalyst composition comprising a divalent nickel salt, a boron hydride and a tertiary organophosphorus compound. In WO 94/25416 a catalyst system for the preparation of $C_4$–$C_{24}$ linear alpha olefins is disclosed, comprising a bis-tetramethylcyclopentadienyl metallocene (the metal being preferably zirconium) and a bulky and labile anion which is substantially non-coordinating (preferably one containing a plurality of boron atoms).

Bridged bis-amido Group 4 (IUPAC 1988 notation) metal compounds are also known, in catalyst systems for the preparation of polyolefins such as polyethylene and polypropylene.

In WO 92/12162 there are disclosed catalyst systems for the polymerization of alpha olefins, comprising as a first component an amido transition metal compound of the general formula (I)

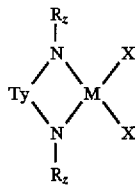

wherein M is zirconium, hafnium or titanium, N is a nitrogen atom having three substituents, X is any univalent anionic ligand, R is a hydrocarbyl, T is a covalent hydrocarbyl bridging group containing a Group IV-A or VI-A element (Deming notation; corresponding to Group 14 and 16 of the IUPAC 1988 notation) such as a silicon radical, y is 1 or 0 and z is 2-y, and as a second component alumoxane. The disclosed effect of this group of catalysts, which does not contain those having in the first component a disilyl, digermyl or distibyl bridging group and those having a second component different from alumoxane, is the production of solid stereoregular polyolefins having a molecular weight well in excess of 100,000.

There has now been found a novel catalyst composition based on bridged bis-amido Group 4 metal compounds which is particularly effective in the oligomerization of lower olefins to produce linear alpha-olefins. Compared to the best catalyst compositions based on metallocenes, this novel composition is distinguished by a highly selective production of the desirable linear alpha-olefins, with high turnover rates under very mild reaction conditions of temperature and pressure. The composition is further distinguished by the ease of preparation of the bis-amido Group 4 metal component from readily available precursors.

SUMMARY OF THE INVENTION

The present invention therefore provides a catalyst composition comprising a compound represented by the general formula (II)

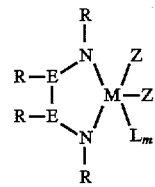

wherein M is zirconium, hafnium or titanium; each N is a three coordinate nitrogen atom; each Y is Si, Ge or Sn; each X is, independently, a hydride or R; each R is, independently, a hydrocarbyl one or more carbon atoms of which may be substituted by an element selected from Si, O, P, N and S; L is a neutral Lewis base and m is a number from 0 to 2; or a dimer thereof; and a second component.

DESCRIPTION OF THE PREFERRED EMBODIMENTS

Preferably each R is independently chosen from the group of $C_1$–$C_{10}$ alkyl, $C_6$–$C_{15}$ aryl, $C_3$–$C_{10}$ cycloalkyl, alkylaryl or $Si(R^1)_3$; each $R^1$ being independently chosen from the group of $C_1$–$C_{10}$ alkyl, $C_6$–$C_{15}$ aryl, $C_3$–$C_{10}$ cycloalkyl or alkylaryl.

Preferably, E is silicon.

Examples of the neutral Lewis base Q are diethylether, tetrahydrofuran, dimethylaniline, aniline, n-butylamine and trimethylphosphine.

The dimer of the compound of formula (II) is according to the general formula (III)

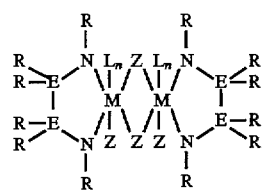

wherein the symbols are as defined above, n being 0 or 1.

Preferred compounds of formula (II) according to the invention are
{1,2-bis(t-butylamide)-tetramethyldisilane}metal dibenzyl, {(Me$_2$SiNCMe$_3$)$_2$}M(CH$_2$Ph)$_2$
{1,2-bis(t-butylamide)-tetramethyldisilane}metal dimethyl, {(Me$_2$SiNCMe$_3$)$_2$}MMe$_2$
{1,2-bis(t-butylamide)-tetramethyldisilane}metal di(n-butyl), {(Me$_2$SiNCMe$_3$)$_2$}M(n-Bu)$_2$ {1,2-bis(t-butylamide)-tetramethyldisilane}metal diphenyl, {(Me$_2$SiNCMe$_3$)$_2$}MPh$_2$ {1,2-bis(t-butylamide)-tetramethyldisilane}metal di(4-methylphenyl), {(Me$_2$SiNCMe$_3$)$_2$}M{CH$_2$(4-Me-Ph)}$_2$ {1,2-bis(t-butylamide)-tetramethyldisilane}metallacyclobutane, {(Me$_2$SiNCMe$_3$)$_2$}{MCH$_2$CH$_2$CH$_2$}

{1,2-bis(t-butylamide)-tetramethyldisilane}metal dihydride, {(Me$_2$SiNCMe$_3$)$_2$}MH$_2$ {1,2-bis(t-amylamide)-tetrametyldisilane}metal dibenzyl, {(Me$_2$SiNCMe$_2$Et)$_2$}M(CH$_2$Ph)$_2$ {1,2-bis(cyclohexylamide)-tetramethyldisilane}metal dibenzyl, {(Me$_2$SiNCy)$_2$}M(CH$_2$Ph)$_2$ {1,2-bis(ethylamide)-tetramethyldisilane}metal dibenzyl, {(Me$_2$SiNEt)$_2$}M(CH$_2$Ph)$_2$ {1,2-bis(phenylamide)-tetramethyldisilane}metal dibenzyl, {(Me$_2$SiNPh)$_2$}M(CH$_2$Ph)$_2$ {1,2-bis(2,6-dimethylphenylamide)-tetramethyldisilane}metal dibenzyl, {(Me$_2$SiN[2,6-Me$_2$Ph])$_2$}M(CH$_2$Ph)$_2$ {1,2-bis(trimethylsilylamide)-tetramethyldisilane}metal dibenzyl, {(Me$_2$SiNSiMe$_3$)$_2$}M(CH$_2$Ph)$_2$ {1,2-bis{tri(t-butyl)silylamide)-tetramethyldisilane}metal dibenzyl, [{(Me$_2$SiNSi(CMe$_3$)$_3$}$_2$]M(CH$_2$Ph)$_2$ {1,2-bis(t-butylamide)-tetraethyldisilane}metal dibenzyl, {(Et$_2$SiNCMe$_3$)$_2$}M(CH$_2$Ph)$_2$ {1,2-bis(t-butylamide)-tetraethyldisilane}metal dimethyl, {(Et$_2$SiNCMe$_3$)$_2$}MMe$_2$ {1,2-bis(t-butylamide)-tetraphenyldisilane}metal dibenzyl, {(Ph$_2$SiNCMe$_3$)$_2$}M(CH$_2$Ph)$_2$ {1,2-bis(t-butylamide)-tetramethyldigermane}metal dibenzyl, {(Me$_2$GeNCMe$_3$)$_2$}M(CH$_2$Ph)$_2$, and {1,2-bis(t-butylamide)-tetramethyldistannane}metal dibenzyl, {(Me$_2$SnNCMe$_3$)$_2$}M(CH$_2$Ph)$_2$ in which the metal (M) is zirconium, hafnium or titanium.

The present invention further comprises a catalyst composition comprising a first component which is a compound according to formula (II) or a dimer thereof, and a second component which is capable of providing a bulky and labile anion [A]$^-$ which anion is substantially non-coordinating under the reaction conditions and contains at least one boron atom.

The first and second component together form an ionic compound of the general formula (IV)

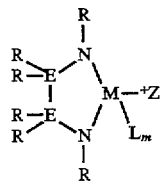

or, of the general formula V

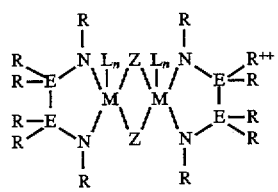

wherein the symbols are as defined above.

Examples of anion [A]$^-$ containing one boron atom are the borates of the general formula [B(R$^2$)$_4$]$^-$, wherein R$^2$ is a hydride, C$_1$–C$_{10}$ alkyl, C$_6$–C$_{15}$ aryl, C$_3$–C$_{10}$ cycloalkyl or alkylaryl, any of which can be substituted by one or more halogens, such as [B(C$_6$F$_5$)$_4$]$^-$, [R$^2$B(C$_6$F$_5$)$_3$]$^-$, [B(FC$_6$H$_4$)$_4$]$^-$, [R$^2$B(FC$_6$H$_4$)$_3$]$^-$, [B{(CF$_3$)$_2$(C$_6$H$_3$)}$_4$]$^-$ and [R$^2$B{(CF$_3$)$_2$(C$_6$H$_3$)}$_3$]$^-$.

Examples of anion [A]$^-$ containing a plurality of boron atoms are the carborates, such as [B$_{11}$CH$_{12}$]$^-$.

The second component can itself be an ionic compound of an anion [A]$^-$ as defined above and a cation. The cation is suitably a proton-donating cation, preferably a tertiary ammonium cation, in particular a trialkylammonium cation such as tri-n-butylammonium, or dimethylanilinium. Alternatively a cation may be used in the second component which is not proton-donating, such as a metal cation e.g. a silver ion, or a triphenyl carbenium ion.

The second component can also be a neutral strongly Lewis acidic compound which is capable of abstracting one of the radicals X of the first component, thereby also contributing an anion [A]$^-$ as defined above.

Preferred second components in the catalytic composition according to the invention are the ionic compounds dimethylanilinium tetrakis(pentafluorophenyl)borate, [PhMe$_2$NH][B(C$_6$F$_5$)$_4$]

tri(n-butyl)ammonium tetrakis(pentafluorophenyl)borate, [Bu$_3$NH][B(C$_6$F$_5$)$_4$]

dimethylanilinium tetrakis(2,3,5,6-tetrafluorophenyl)borate, [PhMe$_2$NH][B(2,3,5,6-C$_6$F$_4$H)$_4$]

dimethylanilinium tetrakis(3,5-bis-trifluoromethylphenyl)borate, [PhMe$_2$NH][B(3,5-(CF$_3$)$_2$—C$_6$H$_3$)$_4$]

dimethylanilinium tetrakis(4-fluorophenyl)borate, [PhMe$_2$NH][B(4-C$_6$H$_4$F)$_4$]

dimethylanilinium tetraphenylborate, [PhMe$_2$NH][B(C$_6$H$_5$)$_4$]

triphenylcarbonium tetrakis(pentafluorophenyl)borate, [Ph$_3$C][B(C$_6$F$_5$)$_4$]

ferrocenium tetrakis(pentafluorophenyl)borate, [(C$_5$H$_5$)$_2$Fe][B(C$_6$F$_5$)$_4$]

silver tetrakis(pentafluorophenyl)borate, [Ag][B(C$_6$F$_5$)$_4$] and tri(n-butyl)ammonium 1-carbodecaborate, [Bu$_3$NH][CB$_{11}$H$_{12}$];

and the neutral, strongly Lewis acidic compounds tris(pentafluorophenyl)borane, B(C$_6$F$_5$)$_3$ tris(2,3,5,6-tetrafluorophenyl)borane, B (2,3,5,6-C$_6$F$_4$)$_3$, and trimethylboron, BMe$_3$.

The compounds of formula (II) according to the invention can be prepared in four steps.

In a first step a compound Cl—ER$_2$ER$_2$—Cl (R and E as defined above) is contacted with at least a four-fold excess of a suitable amine RNH$_2$, followed by separation of the RNH$_3$Cl by-product and removal of the solvent to give a bis-amine product RNHER$_2$ER$_2$NHR.

In a second step the bis-amine product is contacted with a Group 1 metal derivative or with a Gringard derivative of a hydrocarbyl reagent, followed by removal of the solvent to give the Group 1 metal derivative or Grignard derivative of a bis-amide compound RNER$_2$ER$_2$NR.

In a third step a Group 4 metal reactant is contacted in a suitable solvent with the Group 1 metal derivative or Grignard derivative of the bis-amide compound, followed by separation of the salt by-product and purification of the corresponding bis-amide Group 4 metal product.

And in a fourth step the bis-amide Group 4 metal product is contacted in a suitable solvent with a Group 1 metal derivative or with a Grignard derivative of a hydrocarbyl reagent, followed by salt removal and purification of the final compound of formula (II).

Exemplary reactions to prepare boron containing compounds which are suitable for use as the second component are the following.

The neutral, strongly Lewis acidic B(C$_6$F$_5$)$_3$ can be obtained from the reaction of BCl$_3$ with LiC$_6$F$_5$, as described by A. G. Massey and A. J. Park, J. Organomet. Chem. 2 1964 245.

The ionic $[Me_2PhNH]^+[B(C_6F_5)_4]^-$ can be prepared from $B(C_6F_5)_3$ and $LiC_6F_5$, as also described in the Massey and Park publication, to give $Li(OEt_2)_n^+[B(C_6F_5)_4]^-$—which can be converted by reaction with $Me_2PhNHCl$ in dichloromethane to give $[Me_2PhNH]^+[B(C_6F_5)_4]^-$.

$[Ph_3C]^+[B(C_6F_5)_4]^-$ can be prepared by reaction of $Li(OEt_2)_n^+[B(C_6F_5)_4]^-$ with $Ph_3CCl$ in dichloromethane.

The catalyst composition may be formed by mixing together the two components, preferably in a solution in a suitable non-polar solvent such as toluene, benzene, chlorobenzene, an alkane or an alkene, to form a liquid catalyst system. The two components are generally employed in substantially equimolar amounts, although the molar ratio of the first component to the second component may vary within the range of from about 0.1 to about 5.0. Such a quantity of the catalyst system is usually employed in the reaction mixture as to contain from about $10^{-1}$ to about $10^{-7}$ gram atoms, in particular from about $10^{-3}$ to about $10^{-5}$ gram atoms, of the metal per mole of the olefin to be reacted.

The two-component catalyst composition may be formed prior to its introduction to the reaction vessel, or it may be formed in situ.

Although not required for catalytic activity, further components may be added to the catalytic composition according to the invention, for example in order to increase the solubility and/or the stability of the composition. Organo-aluminum compounds in relatively small amounts are efficient scavenging agents.

Examples of such organoaluminum compounds are trimethylaluminum, triethylaluminum, triisopropylaluminum, tri-isobutylaluminum, triphenylaluminum and diethylaluminum chloride.

The complete catalyst composition according to the invention can be used in solution. Alternatively, the catalyst composition can be loaded on a solid carrier, in particular an inorganic oxide such as silica, alumina, silica/alumina, titania, zirconia, magnesia and the like, but resinous support materials such as polyolefins can also be used. Suitable supports are the materials, composed of alumoxane and silica and marketed for example by WITCO GmbH, Bergkamen, Germany.

The invention also provides a process for oligomerizing or co-oligomerizing alpha olefins having a chain length of from 2 to 10 carbon atoms, especially involving ethene, to linear alpha olefins having a chain length of from 4 to 24 carbon atoms, characterized in that the oligomerization reaction is performed in the presence of the catalyst composition according to the invention.

The (co)oligomerization reaction can be carried out in the liquid phase. When the catalyst compositions are loaded on an inert carrier the reaction is heterogeneous and can also be carried out in the gas phase. The reaction can be carried out in batch or in continuous operation.

The (co)oligomerization reaction is generally, although not necessarily, carried out in an inert liquid which is suitably also the solvent for the catalyst components. The reaction is suitably carried out at a moderate temperature, preferably in the range of from about −20° C. to about 150° C., more preferably at about 10° C. to about 100° C. The reaction is suitably carried out under conditions of moderately elevated pressure, preferably in the range of from about 100 to about 10000 kPa, more preferably from about 200 to about 2000 kPa. The optimum conditions of temperature and pressure for a particular reaction system in order to maximize the yield of the desired linear alpha olefins can be readily established by those skilled in the art, but it has been found that temperature between about 20° and about 70° C. and pressures between about 200 and about 1000 kPa are particularly advantageous in this respect with the catalyst systems of the present invention.

The conditions of temperature and pressure are preferably selected to yield a product slate with a 'K factor' within the range of from about 0.3 to about 0.8. The K factor, which is indicative of the relative proportions of the product olefins, is the molar ratio of $[C_{n+2}]/[C_n]$ as calculated from the slope of the graph of log $[C_n mol \%]$ versus n, where n is the number of carbon atoms in the particular product olefin.

The starting reactants can be supplied to the reactor together with an inert diluent, such as nitrogen or helium when the reactant is gaseous, and a liquid solvent, e.g. the same solvent as that of the catalyst components when the reactant is in the liquid form.

The reaction is preferably carried out in the absence of air or moisture.

Reaction times of from 1 minute to 5 hours have been found to be suitable, depending on the activity of the catalyst system and on the reaction conditions. After a suitable reaction time, a conventional catalyst deactivating agent such as water, methanol, or another alcohol may be added if desired to the reaction mixture in order to terminate the reaction. Alternatively, the reaction can simply be terminated by the introduction of air.

The product mixed olefins are preferentially linear alpha olefins having a chain length within the range of 4 to 24 carbon atoms, of which those having between 6 and 10 carbon atoms in the chain are particularly preferred. They may be suitably recovered by distillation and separation techniques known in the art.

If desired, unconverted starting material and oligomeric products having a molecular weight outside the desired molecular weight may be recovered, processed if necessary and recycled to be used as starting material in a subsequent oligomerization reaction.

The invention will be further illustrated by the following examples.

EXAMPLES

1. Preparation of Complexes 1.1 General

All reactions were performed under nitrogen in a Braun MB 200-G dry box or under argon using standard Schlenk techniques. Solvents were dried by refluxing over and distilling from standard reagents. $1,2-Me_4Si_2Cl_2$ and $H_2C(SiMe_2Cl)_2$ were obtained from the reaction of $Me_3SiCl/AlCl_3$ with $Si_2Me_6$ and $H_2C(SiMe_3)_2$, respectively. $PhMe_2NHCl$ was formed by reaction of $PhNMe_2$ and HCl. $Mg(CH_2Ph)Cl$ was obtained from the reaction of $PhCH_2Br$ and Mg; $Mg(CH_2Ph)_2(dioxane)_{0.5}$ was formed on reaction of $Mg(CH_2Ph)Cl$ with dioxane. $Si_2Me_6$, $H_2C(SiMe_3)_2$, $Me_2SiCl_2$, $t-BuNH_2$, $C_6F_5Br$, $BCl_3$, $PhNMe_2$ and $Ph_3CCl$ were obtained from Aldrich. Ether solutions of MeLi and hexane solutions of n-BuLi were obtained from Janssen (Belgium). All new products were characterized by NMR spectroscopy.

1.2 First Component of the Catalyst Composition 1.2.1 Preparation of {1,2-bis(t-butylamide) tetramethyldisilane}-zirconium dibenzyl (Compound 1)

(a) 1,2-Bis(t-butylamine)tetramethyldisilane, $(Me_2SiNHCMe_3)_2$

To a vigorously stirred solution of $1,2-Me_4Si_2Cl_2$ (20.53 g, 110 mmol) in hexane (250 ml) was added a solution of t-BuNH$_2$ (32.9 g, 450 mmol) in hexane (70 ml) using a dropping funnel. On completion of the addition, the white precipitate was removed by filtration, and washed with hexane (500 ml). The supernatant was reduced to dryness giving 27.2 g of (Me$_2$SiNHCMe$_3$)$_2$ (95% yield).

(b) Dilithium 1,2-bis(t-butylamide)tetramethyldisilane, (Me$_2$SiNLiCMe$_3$)$_2$ To a stirred solution of (Me$_2$SiNHCMe$_3$)$_2$ (14.2 g, 54.5 mmol) in hexane (20 ml) was added, via a dropping funnel, 68 ml of a 1.6M n-BuLi solution in hexane (109 mmol). The crude (Me$_2$SiNLiCMe$_3$)$_2$ was obtained as a white solid by removal of the solvent in vacuo.

(c) {1,2-Bis(t-butylamide)tetramethyldisilane}zirconium dichloride, {(Me$_2$SiNCMe$_3$)$_2$}ZrCl$_2$(THF)

To a solution of (Me$_2$SiNHCMe$_3$)$_2$ (30.0 g, 115 mmol) in hexane (200 ml) was added 151 ml of a 1.6M solution of n-BuLi in hexane (242 mmol). The reaction was stirred for 45 min. and the solvent was then removed in vacuo. Toluene (150 ml) was added to the white solid and the resulting suspension introduced (via a transfer tube) into a Schlenk tube containing a vigorously stirred suspension of ZrCl$_4$ (26.8 g, 115 mmol) in toluene (150 ml). The reaction was allowed to warm slowly to room temperature and then stirred for 16 h. The solvent was removed in vacuo and the residue extracted with dichloromethane (2×250 ml). The extract was reduced to dryness and extracted with a dichloromethane/THF mixture (10:1). The extract was again reduced to dryness and extracted with toluene. Colorless microcrystalline {(Me$_2$SiNCMe$_3$)$_2$}ZrCl$_2$(THF) (19.1 g, 40 mmol, 35% yield) was obtained on cooling the toluene solution to -20° C., separation of the crystals by filtration, washing with toluene and drying in vacuo.

(d) Compound 1, {(Me$_2$SiNCMe$_3$)$_2$}Zr(CH$_2$Ph)$_2$

Toluene (20 ml) at -78° C. was added to a Schlenk tube at -78° C. containing a mixture of {(Me$_2$SiNCMe$_3$)$_2$}ZrCl$_2$(THF) (1.72 g, 3.45 mmol) and Mg(CH$_2$Ph)$_2$(dioxane)$_{0.5}$ (1.28 g, 5.18 mmol). The mixture was allowed to warm to room temperature and stirred for 90 min. The solvent was then removed in vacuo, the residue extracted with pentane, and the extract reduced to dryness. Cooling a pentane solution of the crude product to -40° C. afforded 1.50 g (92% yield) of pure yellow crystalline {(Me$_2$SiNCMe$_3$)$_2$}Zr(CH$_2$Ph)$_2$ (1).

1.2.2 Preparation of {1,2-bis(t-butylamide)tetramethyldisilane}-zirconium dimethyl, {(Me$_2$SiNCMe$_3$)$_2$}ZrMe$_2$ (Compound 2)

To a suspension of {(Me$_2$SiNCMe$_3$)$_2$}ZrCl$_2$(THF) (1.90 g, 4.5 mmol) in ether (50 ml) at -78° C. in a Schlenk tube was added by syringe 5.8 ml of a 1.6M solution of MeLi in ether (9.3 mmol). The mixture was allowed to warm slowly to room temperature and the solvent was then removed in vacuo. The residue was then extracted with a small amount of pentane, and the solution cooled to -40° C., to give 0.87 g (51% yield) of pure colorless crystalline {(Me$_2$SiNCMe$_3$)$_2$}ZrMe$_2$(2).

1.2.3 Preparation of {1,2-bis(t-butylamide)tetramethyldisilane}-hafnium dibenzyl (Compound 3)

(a) {1,2-Bis(t-butylamide)tetramethyldisilane}hafnium dichloride, {(Me$_2$SiNCMe$_3$)$_2$}HfCl$_2$(THF)

To a suspension of HfCl$_4$ (4.0 g, 12.5 mmol) in 40 ml of toluene/ether (10:1) was added via a dropping funnel, a solution of (Me$_2$SiNLiCMe$_3$)$_2$ (3.4 g, 12.5 mmol) in toluene/ether (20 ml; 10:1).

The reaction was allowed to warm slowly to room temperature and then stirred for 16 h. The solvent was removed in vacuo and the residue extracted with a dichloromethane/THF mixture (10:1). Reduction of the extract to dryness afforded 5.6 g (81% yield) of crude product. A sample of colorless crystalline {(Me$_2$SiNCMe$_3$)$_2$}—HfCl$_2$(THF) was obtained on cooling a toluene solution.

(b) Compound 3, {(Me$_2$SiNCMe$_3$)$_2$}Hf(CH$_2$Ph)$_2$

To an ether solution of {(Me$_2$SiNCMe$_3$)$_2$}HfCl$_2$(THF) (0.50 g, 1.14 mmol) at -78° C. was added, by syringe, 1.37 ml of a 2.5M solution of Mg(CH$_2$Ph)Cl (3.43 mmol). The mixture was allowed to warm to room temperature, stirred for 1 h, and then reduced to dryness. Extraction with pentane afforded 0.43 g of crude product (71% yield). Crystallization from pentane at -40° C. afforded pure pale yellow {(Me$_2$SiNCMe$_3$)$_2$}Hf(CH$_2$Ph)$_2$ (3). ps 1.2.4 Preparation of {bis(t-butylamide)dimethylsilane} zirconium dibenzyl (Compound 04)

(a) Bis(t-butylamine)dimethylsilane, Me$_2$Si(NHCMe$_3$)$_2$

Reaction of Me$_2$SiCl$_2$ (47.6 g, 370 mmol) with t-BuNH$_2$ (113.3 g, 1550 mmol) in hexane (700 ml) at room temperature, followed by brief reflux (10 min), cooling of the mixture, filtration, and solvent removal from the supernatant afforded an oily product. The Me$_2$Si(NHCMe$_3$)$_2$ was obtained in 98% purity by fractional vacuum distillation.

(b) Dilithium bis(t-butylamide)dimethylsilane, Me$_2$Si(NLiCMe$_3$)$_2$

To a stirred solution of Me$_2$Si(NHCMe$_3$)$_2$ (14.7 g, 72 mmol) in hexane (200 ml) was added, via a dropping funnel, 93.4 ml of a 1.6M n-BuLi solution in hexane (149 mmol). The mixture was then refluxed for 20 minutes, cooled to room temperature, and the solvent removed in vacuo. Dissolution of the crude product in hexane and cooling to -40° C. afforded 14.3 g (3 crops, 92% yield) of colorless crystalline Me$_2$Si(NLiCMe$_3$)$_2$.

(c) {Bis(t-butylamide)dimethylsilane}zirconium dichloride, {Me$_2$Si(NCMe$_3$)$_2$}ZrCl$_2$(THF)$_n$ Toluene (150 ml) at -78° C. was added to a mixture of Me$_2$Si(NLiCMe$_3$)$_2$ (4.01 g, 18.7 mmol) and ZrCl$_4$(THF)$_2$ (7.04 g, 18.7 mmol) at -78° C. and the mixture allowed to warm to room temperature and further stirred for 90 min. The solvent was removed in vacuo and the residue extracted with a mixture of THF and hexane.

The extract was reduced to dryness and then once again extracted with a THF/hexane mixture. Colorless microcrystalline {Me$_2$Si(NCMe$_3$)$_2$}ZrCl$_2$(THF)$_n$ (3 crops, 4.5 g, ca. 50% yield) was obtained on cooling the solution to -40° C. The product is a mixture of {Me$_2$Si(NCMe$_3$)$_2$}ZrCl$_2$(THF)$_2$ and [{Me$_2$Si(NCMe$_3$)$_2$}ZrCl$_2$]$_2$(THF).

(d) Compound 04, {Me$_2$Si(NCMe$_3$)$_2$}Zr(CH$_2$Ph)$_2$

Toluene (40 ml) at -40° C. was added to a Schlenk tube at -40° C. containing a mixture of {Me$_2$Si(NCMe$_3$)$_2$}ZrCl$_2$(THF)$_n$ (0.83 g, 1.7 mmol) and Mg(CH$_2$Ph)$_2$(dioxane)$_{0.5}$ (0.50 g, 1.7 mmol). The mixture was allowed to warm to room temperature and then stirred for 30 min. 30 ml of a hexane/ether mixture (2:1) was added and the reaction mixture was then filtered. The solvent was removed in vacuo, the residue extracted with hexane, and the extract reduced to dryness.

Redissolution of the residue in hexane and cooling to -40° C. afforded 0.47 g (2 crops; 60% yield) of pure yellow crystalline {Me$_2$Si(NCMe$_3$)$_2$}Zr(CH$_2$Ph)$_2$ (1).

1.2.5 Preparation of [bis{(t-butylamide)dimethylsilyl}methane]zirconium dibenzyl (Compound 05)

(a) Bis{(t-butylamine)dimethylsilyl}methane, H$_2$C(Me$_2$SiNHCMe$_3$)$_2$

To a vigorously stirred solution of H$_2$C(SiMe$_2$Cl)$_2$ (12.9 g, 64 mmol) in hexane (150 ml) was added a solution of t-BuNH$_2$ (19.4 g, 265 mmol) in hexane (90 ml) using a dropping funnel. On completion of the addition, the precipitate was removed by filtration and washed with hexane (100 ml). The solvent was removed from the supernatant in vacuo giving 16.6 g of $H_2C(Me_2SiNHCMe_3)_2$ (94% yield).

(b) Dilithium bis{(t-butylamide)dimethylsilyl}methane, $H_2C(Me_2SiNLiCMe_3)_2$

To a stirred solution of $H_2C(Me_2SiNHCMe_3)_2$ (8.30 g, 30 mmol) in hexane (25 ml) was added, via a dropping funnel, 38 ml of a 1.6M n-BuLi solution in hexane (61 mmol). The crude solid $H_2C—(Me_2SiNLiCMe_3)_2$ was obtained by removal of the solvent in vacuo.

(c) [Bis{(t-butylamide)dimethylsilyl}methane]zirconium dichloride, $\{H_2C(SiMe_2NCMe_3)_2\}ZrCl_2(THF)$ To a suspension of $ZrCl_4$ (4.88 g, 20.9 mmol) in 50 ml of toluene/ether (10:1) was added, via a dropping funnel, a solution of $H_2C(Me_2SiNLiCMe_3)_2$ (6.0 g, 12.5 mmol) in toluene/ether (20 ml; 10:1). The reaction was allowed to warm slowly to room temperature, then stirred for 16 h, and the volume was then reduced to 45 ml. The mixture was centrifuged and the supernatant reduced to dryness. The residue was extracted with a dichloromethane/THF mixture (20:1) and the extract reduced to dryness to yield 5.95 g (56% yield) of $\{H_2C(SiMe_2NCMe_3)_2\}ZrCl_2(THF)$.

(d) Compound 05, $\{H_2C(SiMe_2NCMe_3)_2\}Zr(CH_2Ph)_2$

Pentane (20 ml) at $-78°$ C. was added to a Schlenk tube at $-78°$ C. containing a mixture of $\{H_2C(SiMe_2NCMe_3)_2\}ZrCl_2(THF)$ (0.80 g, 1.84 mmol) and $Mg(CH_2Ph)_2(dioxane)_{0.5}$ (0.65 g, 2.58 mmol). The mixture was allowed to warm to room temperature and then stirred for 90 min. The solvent was removed in vacuo and the residue extracted with pentane (2 ml). On cooling the pentane solution to $-40°$ C., 0.36 g (36% yield) of pure yellow crystalline $\{H_2C(SiMe_2NCMe_3)_2\}—Zr(CH_2Ph)_2$ (05) was obtained.

1.3. Second Component of the Catalyst Composition 1.3.1 Tris(pentafluorophenyl)borane, $B(C_6F_5)_3$ (compound A)

$B(C_6F_5)_3$ (A) was obtained from the reaction of $BCl_3$ with $LiC_6F_5$ in hexane, following a literature procedure (A. G. Massey and A. J. Park, *J. Organomet. Chem.* 2 (1964) 245).

1.3.2 Dimethylanilinium tetrakis(pentafluorophenyl)borate, $[Me_2PhNH]^+ [B(C_6F_5)_4]^-$ (compound B)

$[Me_2PhNH]^+[B(C_6F_5)_4]^-$ (B) was synthesized by the metathesis reaction of $Li(OEt_2)_n+ [B(C_6F_5)_4]^-$ with $Me_2PhNHCl$ in dichloromethane. Pure crystalline product was obtained by removal of the lithium chloride by filtration, crystallization of the crude residue from dichloromethane/hexane solution, and ether removal under vacuum (65° C., 3 h). {The $Li(OEt_2)_n+ [B(C_6F_5)_4]^-$ was obtained from the reaction of $LiC_6F_5$ with $B(C_6F_5)_3$ in hexane/ether solution (A. G. Massey and A. J. Park, *J. Organomet. Chem.* 2 (1964) 245)}.

1.3.3 Triphenylcarbonium tetrakis(pentafluorophenyl) borate, $[Ph_3C]^+[B(C_6F_5)_4]^-$ (compound C)

$[Ph_3C]^+[B(C_6F_5)_4]^-$ (C) was formed by reaction of $Li(OEt_2)_n+ [B(C_6F_5)_4]^-$ with $Ph_3CCl$ in dichloromethane. Pure crystalline product was obtained by removal of the lithium chloride by filtration, crystallization of the crude residue from dichloromethane/hexane solution, and ether removal under vacuum (65° C., 3 h).

2 Oligomerization Reactions 2.1 General

The toluene solvent used was dried by refluxing over and distilling from sodium/benzophenone.

2.2 Catalyst Preparation

Catalyst preparation was carried out under nitrogen in a Braun MB 200-G dry box. A mixture of the first component (0.1 or 0.2 mmol) and the second component (0.1 or 0.2 mmol) were placed in a septum bottle and cooled to $-40°$ C. Toluene (10 ml) at $-40°$ C. was added to the stirred mixture, which was then warmed to room temperature over 5 min, giving a yellow solution. The solution was then used immediately for the following step.

2.3 Procedure for Oligomerization

Oligomerizations were performed in a mechanically stirred, jacket-cooled, 1-liter steel autoclave, which, prior to use, was placed under vacuum at 70° C. overnight. Toluene (190 ml) at 25° C. was introduced into the autoclave under vacuum, followed by the catalyst solution. The autoclave was then immediately pressurized with ethylene (ca. 700 kPa) and the temperature and pressure monitored throughout the reaction, while maintaining a constant ethylene pressure. The exotherm, a qualitative measure of the relative activity of the catalysts, was measured as the difference between the starting temperature and the highest temperature reached in the oligomerization.

The oligomerization was terminated after a period of 10–30 minutes by rapidly relieving the pressure in the autoclave and decanting the product mixture using a tap in the base of the autoclave into a collection bottle. Exposure of the mixture to air resulted in rapid deactivation of the catalyst.

2.4 Work-up/analysis

After removal of a sample for GC analysis, the crude product mixture was filtered to remove polyethylene and then placed under vacuum to yield the non-volatile oligomer mixture.

The GC analysis afforded the yields of $C_4$–$C_{30}$ and hexene isomers and was carried out as follows. To a 0.5 ml sample of the crude product mixture, hexylbenzene was added (10 μl) as internal standard. The oligomer product distribution was determined using a HP 5890 gas chromatograph with a CPSIL5 capillary column (50 m×0.25 mm, methylsilicone stationary phase) using helium as carrier gas and flame ionization detection. Response factors for the even linear alpha-olefins and for cis- and trans-2-hexene, cis- and trans-3-hexene, 2-ethyl-1-butene and hexylbenzene (internal standard) were determined using a standard calibration mixture. The yields of the $C_4$–$C_{30}$ olefins obtained from the GC analysis were used to calculate the K factor in oligomerization (via regression analysis).

The turnover rate (TOR) in Table 1, measured in moles of ethylene per hour converted to $C_4$–$C_{30}$ oligomers, per mole of catalyst, is calculated from the formula:

[(weight in g of $C_4$–$C_{30}$ alpha-olefins)]/(moles catalyst)× (reaction time in hours)×28] (28 being the molecular weight of ethylene).

The TOR allows the relative activities of the different catalysts to be compared. The relative amounts of the different hexene isomers found from the GC analysis is a measure of the selectivity of the catalysts towards linear alpha-olefin formation.

After washing the polyethylene with toluene, the recovered polymer was dried under vacuum at 70° C. for three days and the yield then measured. The relative yields of oligomers and PE give a measure of the selectivity of the catalyst towards oligomerization compared to polymerization.

The results are presented in the following Table 1.

TABLE 1

| | | | | | | | | | | $C_6$=: 1H* | $C_6$=: $c_2$H* | $C_6$=: $t_2$H* | $C_6$=: 2EB* |
|---|---|---|---|---|---|---|---|---|---|---|---|---|---|
| Exp. | Cat (mmol) | T (°C.) [exoth] | t (min) | p $C_2$= (kpa) | Yld $C_4$=–$C_{30}$= (g) | TOR $C_4$=–$C_{30}$= (h-1) | Yld 1–$C_6$= (g) | Yld PE (g) | K | (%) | (%) | (%) | (%) |
| 1 | 1A (0.20) | 25 [+22] | 30 | 720 | 17.97 | 6,420 | 2.60 | 1.32 | 0.70 | 99.70 | 0 | 0 | 0.30 |
| 2 | 1A (0.20) | 25 [+9] | 15 | 710 | 15.67 | 11,190 | 2.21 | 1.75 | 0.68 | 99.84 | 0 | 0 | 0.16 |
| 3 | 1A (0.10) | 25 [+5] | 30 | 710 | 11.36 | 8,110 | 1.59 | 0.79 | 0.70 | 99.71 | 0 | 0 | 0.29 |
| 4 | 1A (0.20) | 25 [+13] | 30 | 300 | 17.87 | 6,380 | 2.58 | 0.37 | 0.71 | 99.67 | 0 | 0 | 0.33 |
| 5 | 1A (0.20) | 25 [+5] | 30 | 150 | 9.27 | 3,310 | 1.03 | 0.14 | 0.76 | 99.38 | 0 | 0 | 0.62 |
| 6 | 1A (0.20) | 50 [+12] | 30 | 570 | 4.10 | 1,460 | 0.55 | 0.57 | 0.69 | 98.50 | 0.12 | 0.04 | 1.34 |
| 7 | 2A (0.20) | 25 [+22] | 30 | 720 | 8.98 | 3,210 | 1.03 | 7.66 | 0.77 | 99.00 | 0 | 0.04 | 0.96 |
| 8 | 3A (0.20) | 25 [+3] | 30 | 720 | 0.68 | 240 | 0.15 | 0.02 | 0.60 | 99.98 | 0 | 0 | 0.02 |
| 9 | 1B (0.20) | 25 [+54] | 30 | 710 | 185.9 | 66,400 | 28.26 | 2.33 | 0.72 | 99.61 | 0.11 | 0.05 | 0.23 |
| 10 | 1B (0.10) | 25 [+39] | 10 | 720 | 41.9 | 89,810 | 6.47 | 1.09 | 0.71 | 99.90 | 0.02 | 0 | 0.08 |
| 11 | 2B (0.10) | 25 [+18] | 10 | 720 | 21.8 | 46,710 | 2.51 | 0.48 | 0.72 | 99.93 | 0 | 0 | 0.07 |
| 12 | 3B (0.10) | 25 [+2] | 10 | 720 | 1.7 | 3,580 | 0.32 | 0.10 | 0.65 | 99.50 | 0 | 0 | 0.50 |
| 13 | 1C (.010) | 25 [+62] | 10 | 720 | 141.2 | 302,600 | 18.28 | 3.90 | 0.73 | 98.98 | 0.29 | 0.12 | 0.61 |
| 14 | O4A (.020) | 25 [+2] | 30 | 720 | — | — | — | 0.07 | — | — | — | — | — |
| 15 | O5A (0.20) | 25 [+1] | 30 | 740 | — | — | — | 0.08 | — | — | — | — | — |

Notes
*1H = 1-hexene; $c_2$H = cis-2-hexene; $t_2$H = trans-2-hexene; 2EB = 2-ethyl-1-butene

What is claimed is:

1. A catalyst composition comprising a compound represented by the general formula (II)

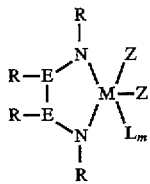

wherein M is zirconium, hafnium or titanium; each N is a three coordinate nitrogen atom; each E is Si, Ge or Sn; each Z is, independently, a hydride or R; each R is, independently, a hydrocarbyl one or more carbon atoms of which may be substituted by an element selected from Si, O, P, N and S; Q is a neutral Lewis base and m is a integer from 0 to 2; or a dimer thereof; and a second component which is capable of providing a bulky and labile anion[A]$^-$, which anion is substantially non-coordinating and contains at least one boron atom.

2. The catalyst composition according to claim 1, wherein each R in the compound according to formula (II) is selected from the group consisting of $C_1$–$C_{10}$ alkyl, $C_6$–$C_{15}$ aryl, $C_3$–$C_{10}$ cycloalkyl, alkylaryl and Si(R$^1$)$_3$; each R$^1$ being independently chosen from the group of $C_1$–$C_{10}$ alkyl, $C_6$–$C_{15}$ aryl, $C_3$–$C_{10}$ cycloalkyl or alkylaryl.

3. The catalyst composition according to claim 1, characterized in that the compound according to formula (II) is selected from the group consisting of {1,2-bis(t-butylamide)-tetramethyldisilane}metal dibenzyl, {(Me$_2$SiNCMe$_3$)$_2$}M(CH$_2$Ph)$_2$, {1,2-bis(t-butylamide)-tetramethyldisilane}metal dimethyl, {(Me$_2$SiNCMe$_3$)$_2$}MMe$_2$, {1,2-bis(t-butylamide)-tetramethyldisilane}metal di(n-butyl), {(Me$_2$SiNCMe$_3$)$_2$}M(n-Bu)$_2$, {1,2-bis(t-butylamide)-tetramethyldisilane}metal diphenyl, {(Me$_2$SiNCMe$_3$)$_2$}MPh$_2$, {1,2-bis(t-butylamide)-tetramethyldisilane}metal di(4-methylphenyl), {(Me$_2$SiNCMe$_3$)$_2$}M{CH$_2$(4-Me-Ph)}$_2$, {1,2-bis(t-butylamide)-tetramethyldisilane}metallacyclobutane, {(Me$_2$SiNCMe$_3$)$_2$}{MCH$_2$CH$_2$CH$_2$}, {1,2-bis(t-butylamide)-tetramethyldisilane}metal dihydride, {(Me$_2$SiNCMe$_3$)$_2$}MH$_2$, {1,2-bis(t-amylamide)-tetramethyldisilane}metal dibenzyl, {(Me$_2$SiNCMe$_2$Et)$_2$}M(CH$_2$Ph)$_2$, {1,2-bis(cyclohexylamide)-tetramethyldisilane}metal dibenzyl, {(Me$_2$SiNCy)$_2$}M(CH$_2$Ph)$_2$, {1,2-bis(ethylamide)-tetramethyldisilane}metal dibenzyl, {(Me$_2$SiNEt)$_2$}M(CH$_2$Ph)$_2$, {1,2-bis(phenylamide)-tetramethyldisilane}metal dibenzyl, {(Me$_2$SiNPh)$_2$}M(CH$_2$Ph)$_2$, {1,2-bis(2,6-dimethylphenylamide)-tetramethyldisilane}metal dibenzyl, {Me$_2$SiN[2,6-Me$_2$-{Ph}]$_2$}M(CH$_2$Ph)$_2$, {1,2-bis(trimethylsilylamide)-tetramethyldisilane}metal dibenzyl, {(Me$_2$SiNSiMe$_3$)$_2$}M(CH$_2$Ph)$_2$, {1,2-bis{tri(t-butyl)silylamide)-tetramethyldisilane}metal dibenzyl, [{(Me$_2$SiNSi(CMe$_3$)$_3$}$_2$]M(CH$_2$Ph)$_2$, {1,2-bis(t-butylamide)-tetraethyldisilane}metal dibenzyl, {(Et$_2$SiNCMe$_3$)$_2$}M(CH$_2$Ph)$_2$, {1,2-bis(t-butylamide)-tetraethyldisilane}metal dimethyl, {(Et$_2$SiNCMe$_3$)$_2$}MMe$_2$, {1,2-bis(t-butylamide)-tetraphenyldisilane}metal dibenzyl, {(Ph$_2$SiNCMe$_3$)$_2$}M(CH$_2$Ph)$_2$, {1,2-bis(t-butylamide)-tetramethyldigermane}metal dibenzyl, {(Me$_2$GeNCMe$_3$)$_2$}M(CH$_2$Ph)$_2$, and {1,2-bis(t-butylamide)-tetramethyldistannane}metal dibenzyl, {(Me$_2$SnNCMe$_3$)$_2$}M(CH$_2$Ph)$_2$, in which the metal (M) is zirconium, hafnium or titanium.

4. The catalyst composition according to claim 1, characterized in that E is silicon.

5. The catalyst composition according to claim 1, wherein said composition is loaded on a solid carrier selected from the group consisting of silica, alumina, silica/alumina, titania, zirconia, magnesia, a resinous support material, and mixtures thereof.

6. The catalyst composition according to claim 1, characterized in that the anion [A]$^-$ is a borate of the general formula [B(R$^2$)$_4$]$^-$, wherein R$^2$ is a hydride, C$_1$–C$_{10}$ alkyl, C$_6$–C$_{15}$ aryl, C$_3$–C$_{10}$ cycloalkyl or alkylaryl, any of which can be substituted by one or more halogens.

7. The catalyst composition according to claim 1, wherein said composition further comprises an organoaluminum compound.

8. The catalyst composition according to claim 1, characterized in that the anion [A]$^-$ is a carborate.

9. The catalyst composition according to claim 1, characterized in that the second component is selected from the group consisting of dimethylanilinium tetrakis(pentafluorophenyl)borate, [PhMe$_2$NH][B(C$_6$F$_5$)$_4$], tri(n-butyl)ammonium tetrakis(pentafluorophenyl)borate, [Bu$_3$NH][B(C$_6$F$_5$)$_4$], dimethylanilinium tetrakis(2,3,5,6-tetrafluorophenyl)borate, [PhMe$_2$NH][B(2,3,5,6-C$_6$F$_4$H)$_4$], dimethylanilinium tetrakis(3,5-bis-trifluoromethylphenyl)borate, [PhMe$_2$NH][B(3,5-(CF$_3$)$_2$—C$_6$H$_3$)$_4$], dimethylanilinium tetrakis(4-fluorophenyl)borate, [PhMe$_2$NH][B(4-C$_6$H$_4$F)$_4$], dimethylanilinium tetraphenylborate, [PhMe$_2$NH][B(C$_6$H$_5$)$_4$], triphenylcarbonium tetrakis(pentafluorophenyl)borate, [Ph$_3$C][B(C$_6$F$_5$)$_4$], ferrocenium tetrakis(pentafluorophenyl)borate, [(C$_5$H$_5$)$_2$Fe][B(C$_6$F$_5$)$_4$], silver tetrakis(pentafluorophenyl)borate, [Ag][B(C$_6$F$_5$)$_4$], tri(n-butyl)ammonium 1-carbodecaborate, tris(pentafluorophenyl)borane, B(C$_6$F$_5$)$_3$, tris(2,3,5,6-tetrafluorophenyl)borane, B(2,3,5,6-C$_6$F$_4$)$_3$, and trimethylboron, BMe$_3$.

\* \* \* \* \*